US00PP13301P2

(12) United States Plant Patent
Olesen et al.

(10) Patent No.: US PP13,301 P2
(45) Date of Patent: Dec. 3, 2002

(54) MINIATURE ROSE PLANT NAMED 'POULNIL'

(76) Inventors: L. Pernille Olesen, Hillerødvejen 49, DK-3480 Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 193 days.

(21) Appl. No.: 09/658,828

(22) Filed: Sep. 8, 2000

(51) Int. Cl.[7] ..... A01H 5/00
(52) U.S. Cl. ..... Plt./116; Plt./123
(58) Field of Search ..... Plt./116, 118, 121, Plt./123, 128, 125

(56) References Cited

U.S. PATENT DOCUMENTS

PP11,598 P * 10/2000 Olesen et al. ..... Plt./143

OTHER PUBLICATIONS

Community Plant Variety Office. "Certificate on the Grant of Community Plant Variety Rights" Jun. 19, 2000. 6 pages. EU.

UPOV–ROM, 2001/03, Plant Variety Database, GTI Jouve Retrieval Software,2 citations for 'Poulnil'.*

* cited by examiner

*Primary Examiner*—Howard J. Locker

(57) ABSTRACT

A new miniature rose plant which has abundant, yellow-pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between an unnamed seedling and an unnamed seedling. The two parents were crossed and the resulting seeds were planted in a controlled environment. The new variety is named 'POULnil'.

The new rose may be distinguished from its seed parent, an unnamed seedling, by the following characteristics:

The unnamed seed parent has yellow blooms, while POULnil has lighter, yellow-pink flowers.

The new variety may be distinguished from its pollen parent, an unnamed seedling, created by the same inventors, by the following combination of characteristics:

1. The unnamed pollen parent is smaller in habit than 'POULnil'.
2. The unnamed pollen parent has warm yellow blooms, while those of 'POULnil' are more pink in color.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

The combination of qualities of this variety represents significant improvement over previously available commercial cultivars of this type and distinguishes 'POULnil' from all other varieties of which we are aware. As part of their rose development program, L. Pernille Olesen and Mogens N. Olesen germinated the seeds from the aforementioned hybridization and conducted evaluations on the resulting seedlings in a controlled environment in Fredensborg, Denmark.

'POULnil' was selected by the inventors as a single plant from the progeny of the hybridization in May of 1998.

Asexual reproduction of 'POULnil' by cuttings and traditional budding onto *Rosa multiflora* understock was first done by L. Pernille and Mogens N. Olesen in October Of 1998 in their nursery in Fredensborg, Denmark. This initial and other subsequent propagations conducted in controlled environments have demonstrated that the characteristics of 'POULnil' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULnil'. Specifically illustrated in SHEET 1:

1. Stem showing branching and the attachment of leaves, buds, and peduncles;
2. Flower bud, partially opened bud, and open bloom;
3. Flower petals, detached;
4. Sepals and pedicel;
5. Two stems, one bare, exhibiting thorns;
6. Leaves.

DETAILED DESCRIPTION OF THE VARIETY

The following is a description of 'POULnil', as observed in its growth in glasshouses in Half Moon Bay, Calif. Color references are made using The Royal Horticultural Society (London, England) Colour Chart, 1995, except where common terms of color are used.

For a comparison, several physical characteristics of the rose variety 'POULjoey', a miniature rose variety from the same inventors described and illustrated in U.S. Plant Pat. No. 11,598, Oct. 24, 2000, are compared to 'POULnil' in Chart 1.

CHART 1

| | 'POULnil' | 'POULjoey' |
|---|---|---|
| Petalage | Semi-double; 16 to 19 petals. | Very double; 55 to 65 petals. |
| Petal Color, Upper Surface | Red-Purple Group 62D at margins, Red Group 36D in middle and basal zones, all with a faint overlay of Green-Yellow Group 1B–C. | A blend of Orange Group 28C and Red Group 39B–C. |
| Petal Color, Lower Surface | Red-Purple Group 62C.. | A blend of Red Group 54B and Orange-Red Group 34C. |

Parents: Unnamed seedling×Unnamed seedling.
Classification:
*Botanical.*—*Rosa hybrida.*
*Commercial.*—Miniature.

FLOWER AND FLOWER BUD

Blooming habit:
Flower bud:
*Size.*—Upon opening, 26 mm–28 mm in length from base of receptacle to end of bud.
*Bud form.*—Pointed ovoid.
*Bud color.*—As sepals unfold orange-red group 31A–B, orange-red group 31A at ¼ opening.
*Sepals.*—Outer surface is Green Group 143C; inner surface is Yellow-Green 144A–B. Moderate foliaceous appendages on three of the five sepals. Surfaces of sepals slightly pubescent. Stipitate glands are present in limited quantities.
*Receptacle.*—Surface: Smooth and glossy. Shape: Urn-shaped. Size: 6 mm (h)×5 mm (w). Color: Yellow-Green Group 144B, with intonations of Yellow-Green Group 144A.
*Peduncle.*—Surface: Smooth, with stipitate glands in limited quantities. Length: 50 to 60 mm average length. Color: Yellow-Green Group 144A. Strength: Upright.
*Borne.*—Generally with one bud per flowering stem.
Flower bloom:
*Fragrance.*—Light.
*Duration.*—As a pot plant, flowers last from 6 to 8 days. As a cut flower 4 to 5 days.
*Size.*—Medium for a 15.5 cm pot rose. Average flower diameter is 65 to 75 mm when open.
*Form.*—Shape of flower when viewed from the side: Upon opening, upper part: Convex. Upon opening, lower part: Convex. Open flower, upper part: Flattened convex. Open flower, lower part: Flattened convex.
*Petalage.*—Average range: 16 to 19 petals under normal conditions with few or no petaloids.
Color:
*Upon opening, petals.*—Outermost petals: Upper Surface: Red-Purple Group 62D at margins, Red Group 36D in middle and basal zones, all with a faint overlay of Green-Yellow Group 1B–C. Reverse Side: Red Group 49B. Innermost petals: Upper Surface: Red-Purple Group 62D at margins, Red Group 36D in middle and basal zones, all with a faint overlay of Green-Yellow Group 1B–C. Reverse Side: Red-Purple Group 62C.
*Upon opening, basal petal spots.*—Outermost petals: Outer Side: Yellow Group 2C–D. Inner Side: Yellow Group 3B, with intonations of Yellow Group 2C–D. Innermost petals: Outer Side: White Group 155C, Yellow Group 2D. Inner Side: Yellow Group 2C–D.
*After opening, petals.*—Outermost petals: Upper Surface: Red-Purple Group 62D at margins, Red Group 36D in middle and basal zones, all with a faint overlay of Green-Yellow Group 1B–C. Reverse Side: Red-Purple Group 62C. Innermost petals: Upper Surface: Marginal zone Red Group 56C, basal and middle zones 65A–B. Reverse Side: Marginal Zone, Red-Purple Group 65B, middle and basal zones, Red-Purple Group 65C.
*After opening, basal petal spots.*—Outermost petals: Outer Side: Green-Yellow Group 1C. Inner Side: Yellow Group 3A. Innermost petals: Outer Side: Green-Yellow Group 1C. Inner Side: Yellow Group 2A.
General tonality: On open flower Red-Purple Group 62D at margins, Red Group 36D in middle and basal zones, all with a faint overlay of Green-Yellow Group 1B–C. No change in the general tonality at the end of the 6th day. Afterwards, general tonality is Red-Purple Group 65D.
Petals:
*Petal reflex.*—Slight.
*Petal edge.*—Point in center of margin.
*Shape.*—Predominantly rounded deltoid; some round.
*Petaloids.*—Occasionally 2 to 4; often none are present.
*Thickness.*—Average.
*Arrangement.*—Imbricated.
Reproductive organs:
*Pollen.*—Color: None observed.
*Anthers.*—Size: Medium. Color: Yellow Group 2C with intonations of Greyed-Orange Group 177A. Abundance: Very abundant.
*Filaments.*—Color: Yellow Group 5A–B.
*Stigmas.*—Slightly inferior in location to anthers. Color: Greyed-Yellow Group 160C.
*Styles.*—Color: Greyed-Red Group 181B.
*Hips.*—None noted.

PLANT

Plant growth: Vigorous, compact. When grown as a 15.5 cm pot plant (as is typical in the commercial production of the variety), the average height of the plant itself is 20 to 25 cm and the average width is 22 to 27 cm.
Stems:
*Color.*—Young wood: Yellow-Green Group 144A. Older wood: Yellow-Green Group 144A.
*Prickles.*—Incidence: Few, occurring primarily on lower 10 to 15 cm of plant stems. Size: Average length: 4 mm–5 mm. Color: Greyed-Yellow Group 160C. Shape: Linear.
*Surface.*—Young wood: Smooth. Older wood: Smooth.
Plant foliage: Normal number of leaflets on leaves in middle of the stem: 5 leaflets.
*Leaf size.*—31 mm (l)×28 mm (w).
*Abundance.*—Average.
*Color.*—Upper Leaf Surface: Green Group 139A. Lower Leaf Surface: Green Group 137C. Juvenile foliage: Upper Surface: Green Group 137A. Lower Surface: Green Group 138B. Anthocyanin intonation: Location: Marginal zones of upper and lower surfaces of juvenile foliage. Color: Greyed-Purple Group 185A.

Plant leaves and leaflets:

*Stipules.*—Size: Small. Color: Interior of stipule is Yellow-Green Group 144C–D; points of stipule are 144A–B.

*Petiole.*—Length: 15 mm–18 mm. Color: Yellow-Green Group 144B. Underneath: Yellow-Green Group 144B. Margins: Raised margins of Greyed-Purple Group 185A.

*Rachis.*—Color: Yellow-Green Group 144B. Underneath: Yellow-Green Group 133B. Margins: Raised margins of Yellow-Green Group 144A.

*Leaflet.*—Edge: Serrated. Shape: Ovate.

*Texture.*—Moderately glossy, moderately thick.

Disease resistance: Average resistance to mildew, black spot, and Botrytis under normal growing conditions in Half Moon Bay, Calif.

Cold hardiness: 'POULnil' has been found to be resistant to damage from cold, heat and drought damage in USDA Zone 7.

We claim:

1. A new and distinct variety of rose plant of the miniature class, substantially as herein illustrated and described as a distinct and novel rose variety due to its abundant flowers, vigorous and compact growth, year round flowering under glasshouse conditions, suitability for production from softwood cuttings in pots, and durable flowers and foliage which make the variety suitable for distribution in the floral industry.

* * * * *

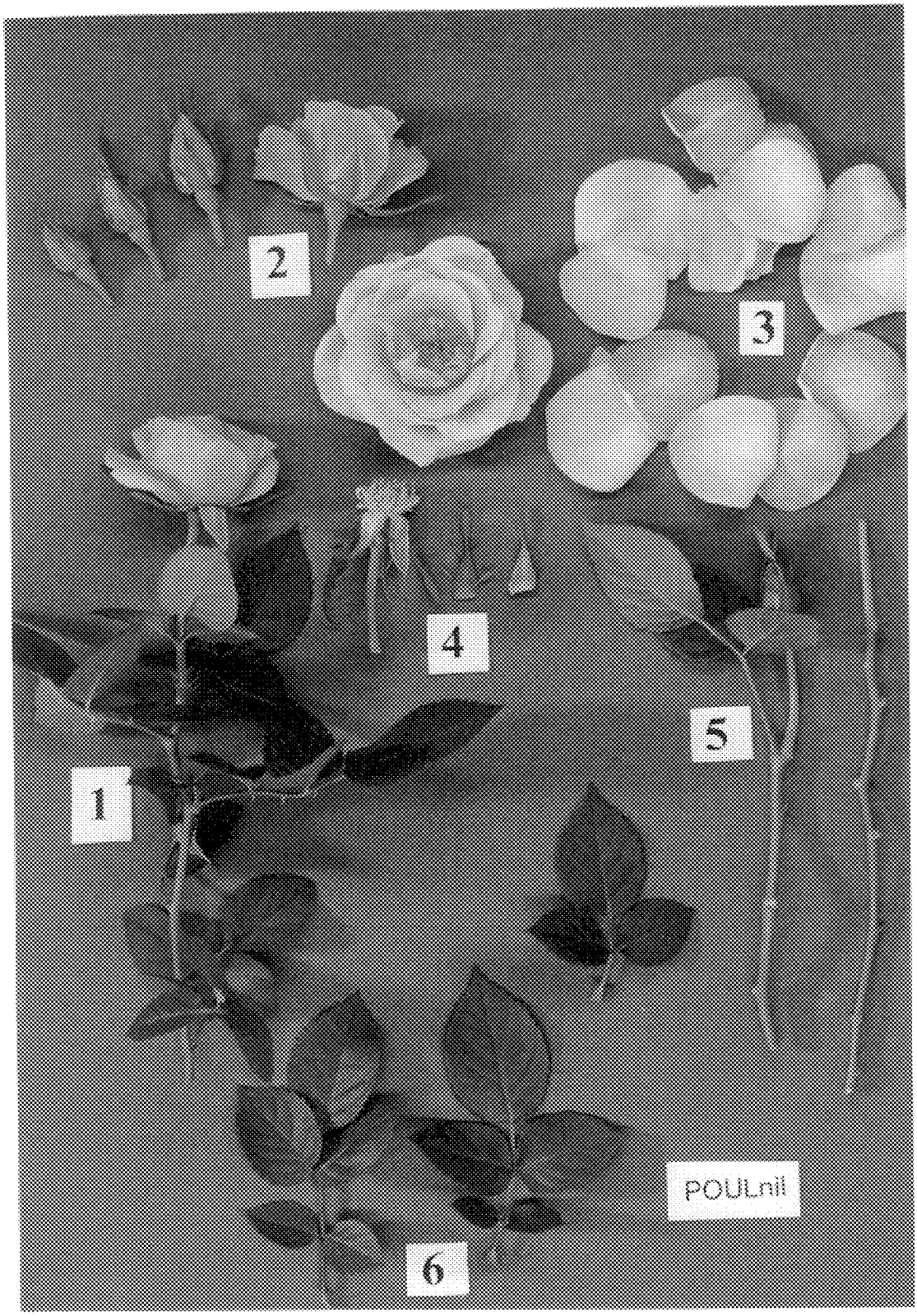
2
3
4
5
1
POULnil
6